United States Patent [19]

Kellan

[11] Patent Number: 5,709,220
[45] Date of Patent: *Jan. 20, 1998

[54] HEAD STABILIZER AND SUPERIOR RECTUS BRIDLE SUTURE FIXATOR DEVICE FOR USE IN EYE SURGERY AND METHODS THEREFOR

[76] Inventor: Robert E. Kellan, 60 East St., Suite 1100, Methuen, Mass. 01844

[*] Notice: The term of this patent shall not extend beyond the expiration date of Pat. No. 5,361,780.

[21] Appl. No.: 808,724

[22] Filed: Dec. 17, 1991

[51] Int. Cl.⁶ .................................. A61B 19/00
[52] U.S. Cl. ................. 128/849; 128/869; 128/876
[58] Field of Search ............... 128/DIG. 26, 845, 128/846, 849, 853, 857, 858, 869, 870, 876; 602/17, 74

[56] References Cited

U.S. PATENT DOCUMENTS

| | | | |
|---|---|---|---|
| 2,492,383 | 12/1949 | Jones | 128/869 X |
| 3,086,529 | 4/1963 | Munz et al. | |
| 3,190,444 | 6/1965 | Kelson | |
| 3,315,671 | 4/1967 | Creelman | |
| 3,358,141 | 12/1967 | Hoffmann et al. | |
| 3,469,268 | 9/1969 | Phillips | |
| 3,586,001 | 6/1971 | Sanderson | |
| 3,889,668 | 6/1975 | Ochs et al. | |
| 3,897,777 | 8/1975 | Morrison | 128/869 |
| 4,058,112 | 11/1977 | Johnson | 128/845 |
| 4,108,170 | 8/1978 | Spann | |
| 4,182,322 | 1/1980 | Miller | 128/869 |
| 4,299,209 | 11/1981 | Behrens et al. | |
| 4,550,713 | 11/1985 | Hyman | 128/849 X |
| 4,665,566 | 5/1987 | Garrow | 128/DIG. 26 X |
| 4,700,691 | 10/1987 | Tari et al. | 128/869 |
| 4,707,031 | 11/1987 | Meistoell | 128/869 X |
| 5,015,251 | 5/1991 | Cherubini | |
| 5,027,833 | 7/1991 | Calkin | 128/869 X |
| 5,042,507 | 8/1991 | Dowdy | 128/849 |
| 5,081,665 | 1/1992 | Kostich | 128/869 X |
| 5,361,780 | 11/1994 | Kellan | 128/849 |

FOREIGN PATENT DOCUMENTS

| | | | |
|---|---|---|---|
| 725072 | 3/1955 | United Kingdom | 128/869 |
| 8101513 | 6/1981 | WIPO | 128/869 |

Primary Examiner—Michael A. Brown

[57] ABSTRACT

A head stabilizer device includes a strap to be secured laterally around the head of a patient lying in a supine position on an operating table and around the operating table to hold the patient's head in a stabilized, non-moving position during eye surgery. The strap carries a fixation surface to be disposed along the patient's forehead for fixating a superior rectus bridle suture with controlled tension to optimally position the eye for surgery while allowing the tension and fixation site for the superior rectus bridle suture to be adjusted during surgery to reposition the eye.

5 Claims, 2 Drawing Sheets

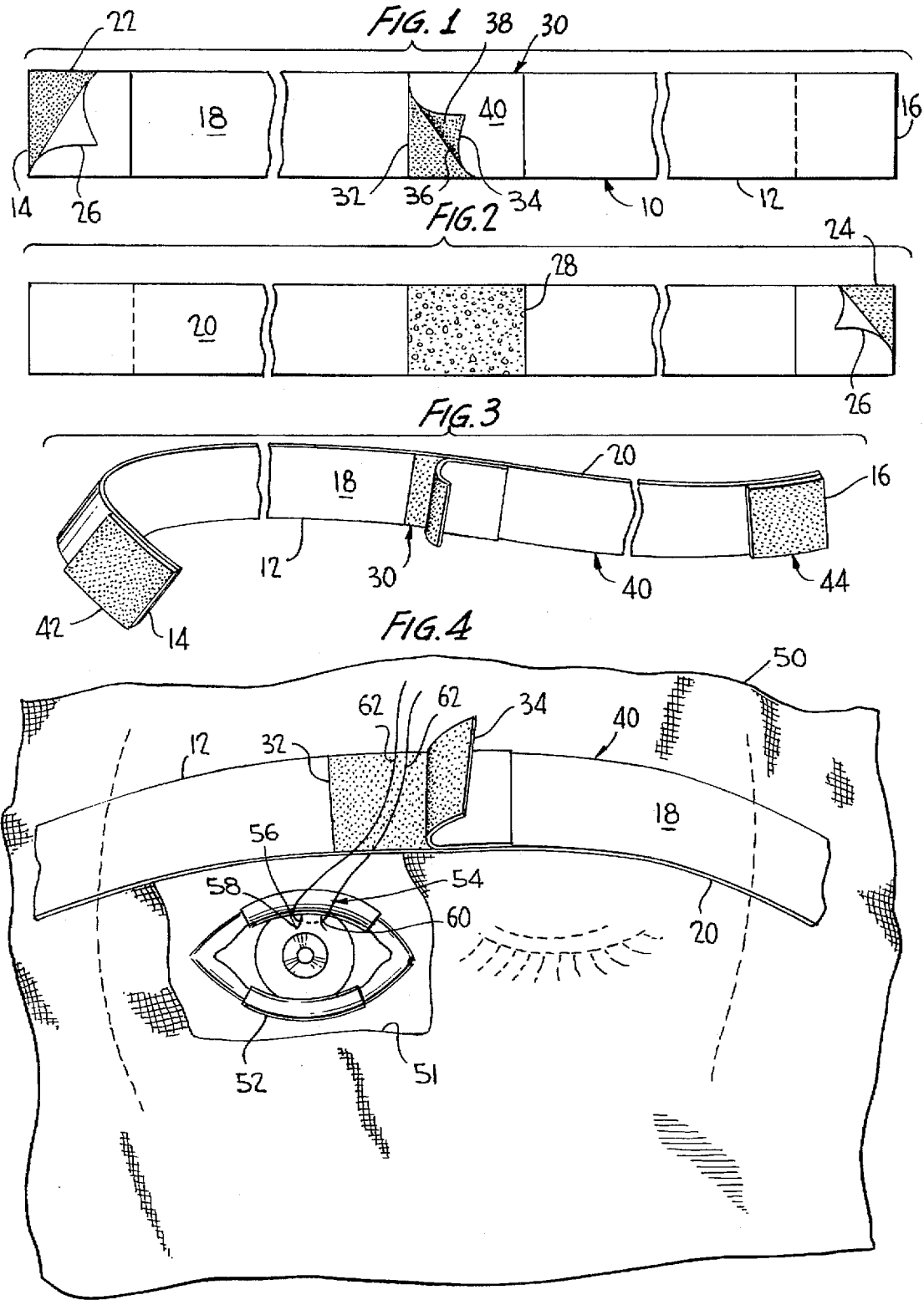

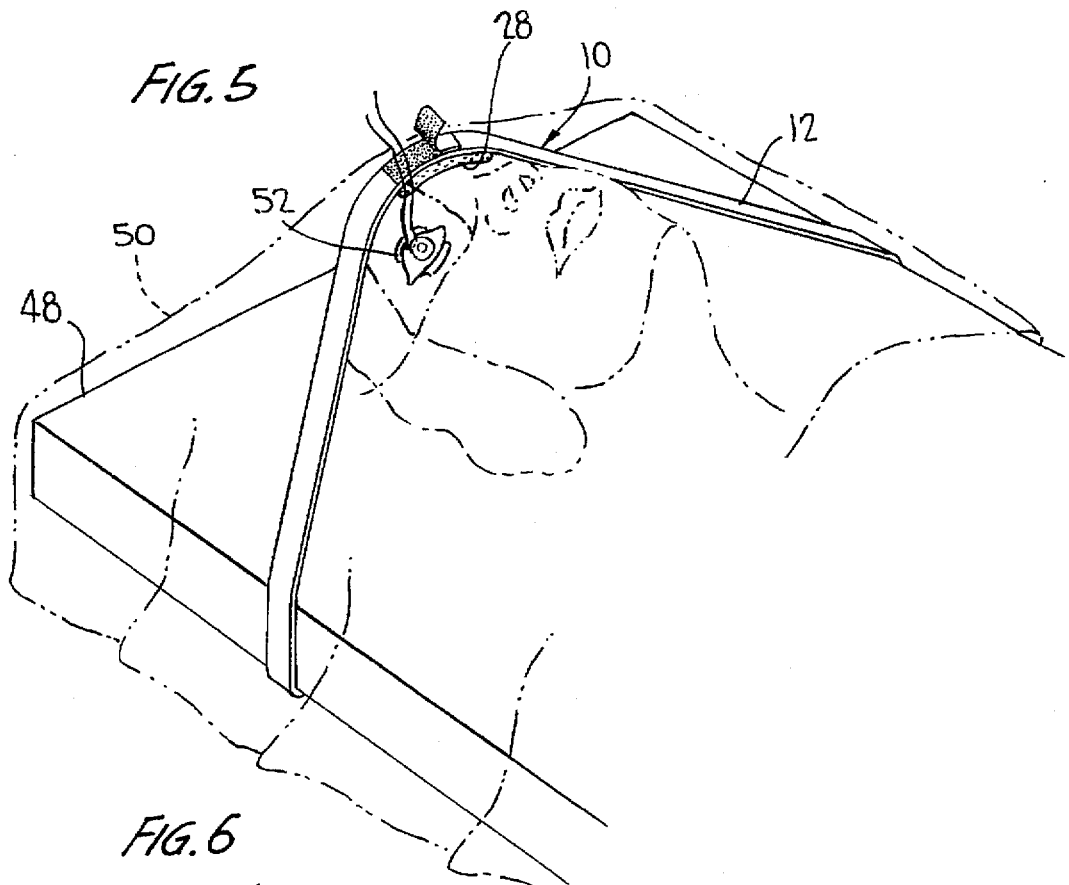
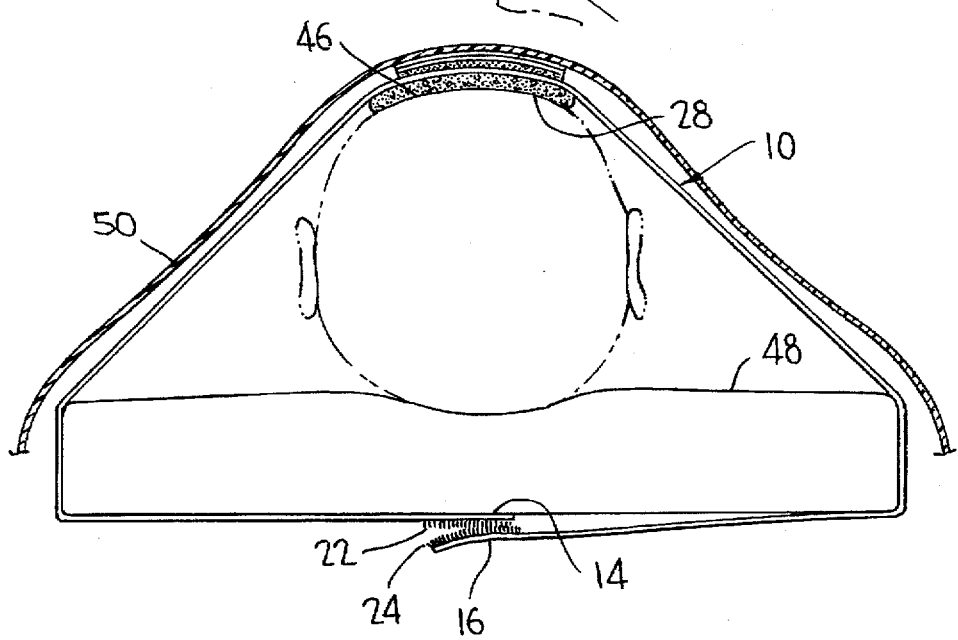

HEAD STABILIZER AND SUPERIOR RECTUS BRIDLE SUTURE FIXATOR DEVICE FOR USE IN EYE SURGERY AND METHODS THEREFOR

BACKGROUND OF THE INVENTION

1. Field of the Invention

The present invention relates to eye surgery and, more particularly, to a head stabilizer and superior rectus bridle suture fixator device particularly useful in cataract surgery and methods of performing cataract surgery while stabilizing a patient's head and fixating superior rectus bridle sutures.

2. Discussion of the Prior Art

During eye surgery, a patient typically lies, on an operating table with the back of the patient's head supported on a head support part of or associated with the operating table. A surgeon is usually positioned adjacent the head support to approach the patient's eye from the top of the patient's head and over the frontal bone, or forehead, of the patient. The head support prevents some movement of the patient's head during surgery; however, the patient's head can still move during surgery due to forces applied by the surgeon or due to movement by the patient since the patient is usually anesthetized locally and, therefore, capable of voluntary head motion. Movement of the patient's head is undesirable during eye surgery and, in particular, cataract surgery, and can lead to substantial complications. During cataract surgery, various surgical instruments are inserted in the eye including instruments for forming an incision in the conjunctiva and limbus, for performing a capsulotomy, for removing the cataractous natural lens, for irrigating and aspirating, and for inserting a lens implant. Accordingly, the patient's head must be held stable to allow precise positioning of the surgical instruments and to avoid damage to surrounding tissue and eye structure from inadvertent contact with the instruments caused by unexpected head movements. Even slight movements of the patient's head during cataract surgery can increase the difficulty of the surgical procedure and can produce adverse consequences due to the precision of the procedure and the small space in which the surgeon has to operate. When the phacoemulsification technique for lens removal is employed, lens tissue is fragmented with an instrument having an ultra-sound tip moving at very high speeds, i.e. approximately 40,000 times per second, while fragmented tissue is aspirated through the instrument. Movement of the patient's head can impair accurate placement of the phacoemulsifier probe resulting in destruction of and/or aspiration of healthy eye tissue. Furthermore, it may be desirable in certain instances for the patient's head to be tilted laterally to one side or the other during surgery to optimize exposure of the eye; however, such head positions are usually precluded during cataract surgery due to the inability to maintain the patient's head at the desired angle for the duration of the surgical procedure, particularly when the patient is anesthetized locally. Although head stabilizers for surgical use have been proposed, no effective head stabilizers have been proposed for use in eye or cataract surgery.

It is also important during eye surgery to immobilize the eye itself; and, accordingly, a bridle suture is usually employed for holding the superior rectus muscle of the eye to restrain and optimally position the eye for surgery. The superior rectus bridle suture is conventionally formed by inserting a needle with a length of suture material attached thereto through the conjunctiva at an entry point located 8 to 10mm behind the limbus and adjacent a lateral side of the superior rectus, grasping the superior rectus with a muscle forceps, lifting the superior rectus outwardly from the eye, inserting the needle under the raised superior rectus and pulling the needle and suture material through the conjunctiva to exit the eye at a point disposed adjacent an opposing lateral side of the superior rectus. The suture material thusly extends under the superior rectus transversely, or laterally, with ends of the suture material extending from the entry and exit points externally of the eye. The ends of the suture material are grasped and pulled with desired tension in the direction of the patient's forehead such that the superior rectus is lifted by the bridle suture to optimally position the eye in the optic orbit. The superior rectus and, therefore, the eye, is conventionally held in a desired position by securing the ends of the suture material with clamps or tape to a surgical drape in the surgical field or by securing the ends of the suture material to a clamp that is positioned to allow the weight of the clamp to provide tension. Conventional methods for securing the superior rectus bridle suture possess numerous disadvantages including the inability to control the position of the eye, failure to maintain uniform tension on the superior rectus during the surgical procedure, difficulty in changing the position of the eye during the surgical procedure, possible obstruction of the surgical field and decreased reliability due to the increased opportunity for the ends of the suture material to move or become disengaged from the securement site.

There is a great need for head restraints for many other eye procedures performed under local anesthesia such as, for example, photorefractive keratectomy wherein a laser is used to modify corneal curvature to eliminate refractive errors such that any movement of the head during the procedure may compromise the results.

SUMMARY OF THE INVENTION

Accordingly, it is a primary object of the present invention to overcome the aforementioned disadvantages of the prior art by allowing a surgeon to position a patient's head for optimal exposure during eye surgery and keep the head from moving during the surgical procedure.

Another object of the present invention is to facilitate eye surgery by stabilizing a patient's head to prevent lateral and forward movements.

A further object of the present invention is to provide a method of performing eye surgery including fixating a superior rectus bridle suture on a bridle suture fixator with controlled, uniform tension and while allowing the tension and fixation site for the superior rectus bridle suture to be easily adjusted during surgery to reposition a patient's eye.

An additional object of the present invention is to provide a superior rectus bridle suture fixator to be disposed along the forehead of a patient undergoing eye surgery for fixating a superior rectus bridle suture securely thereon without the need for clamps, tape or other extraneous securing devices.

Yet another object of the present invention is to provide a bridle suture fixator on a head stabilizer for fixating a superior rectus bridle suture while stabilizing a patient's head during cataract surgery.

The present invention has another object in providing a system for performing eye surgery including an operating table for supporting a patient in a supine position, a surgical drape for covering the patient's head with an opening exposing an eye to be operated, and a head stabilizer device for holding the patient's head in a stabilized non-moving position, the head stabilizer device extending across the forehead of the patient and around the operating table and having opposing end carrying fasteners for securing the opposing ends together to hold the head of the patient against the operating table.

Some of the advantages of the present invention are that surgical instruments can be positioned in the eye during cataract surgery with enhanced precision and safety, damage to healthy eye tissue and structures due to inadvertent head movement is minimized, superior rectus bridle sutures can be fixated during eye surgery with precision and reliability and without obstruction of the surgical field, a patient's head can be stabilized during cataract surgery in a simple and comfortable manner, the superior rectus bridle suture fixator and head stabilizer are compatible for use with diverse sizes and types of operating tables or head supports and can be economically disposable for single patient use.

The present invention is generally characterized in a head stabilizer and superior rectus bridle suture fixator including a strap to be positioned over a patient's forehead to laterally encircle the patient's head and an operating table supporting the patient's head for surgery. The strap includes opposing ends having fasteners thereon allowing the ends to be releasably secured together in overlapping engagement to maintain the strap in a position tightly encircling the patient's head and the operating table. A superior rectus bridle suture fixator on the strap includes an adhesive fixation surface to be disposed along the patient's forehead and a cover removably secured on the fixation surface for selectively exposing at least a portion of the fixation surface to allow a superior rectus bridle suture formed in the patient's eye to be fixated on the fixation surface with controlled, uniform tension to position the eye for surgery and to permit the tension and/or fixation site for the bridle suture to be adjusted during surgery to reposition the eye.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 1 is a broken top plan view of a head stabilizer and superior rectus bridle suture fixator device according to the present invention.

FIG. 2 is a broken bottom plan view of the head stabilizer and superior rectus bridle suture fixator device of FIG. 1.

FIG. 3 is a perspective view of another embodiment of a head stabilizer and superior rectus bridle suture fixator device according to the present invention.

FIG. 4 is a broken top view of the head stabilizer and superior rectus bridle suture fixator device of the present invention in use over a surgical drape.

FIG. 5 is a perspective view of the head stabilizer and superior rectus bridle suture fixator device of the present invention in use under a surgical drape.

FIG. 6 is an end view of the head stabilizer and superior rectus bridle suture fixator device of the present invention as used in FIG. 5.

DESCRIPTION OF THE PREFERRED EMBODIMENTS

As shown in FIGS. 1 and 2, a head stabilizer and superior rectus bridle suture fixator device 10 according to the present invention includes a strap, or strip, of material 12 extending lengthwise with a substantially uniform width between opposing free ends 14 and 16. An upper or proximal surface 18 of the strap 12 is separated from a lower or distal surface 20 thereof by a minimal thickness substantially uniform along the length of the strap. A layer 22 of activated adhesive is provided as a fastener on the upper surface 18 adjacent the end 14, and a layer 24 of activated adhesive is provided as a fastener on the lower surface 20 adjacent the end 16 for adhesively engaging the layer 22. Protective release sheets 26 are disposed over and completely cover the adhesive layers 22 and 24, respectively, with the release sheets 26 being removably secured on the layers 22 and 24. The release sheets 26 can be manually peeled away from the strap 12 with a force sufficient to overcome the bond between the release sheets and the adhesive layers 22 and 24, respectively, to selectively expose the adhesive layers 22 and 24. A cushion, or pad, 28 is secured on the lower surface 20 centrally between the ends 14 and 16 for positioning over the frontal bone, or forehead, of a patient lying upon an operating table with the back of the patient's head supported on the operating table. The length of the strap 12 is selected to allow the ends 14 and 16 to be positioned in overlapping arrangement beneath the operating table when the strap tightly encircles the patient's head and the operating table laterally. Removal of the release sheets 26 to reveal the adhesive layers 22 and 24 allows the ends 14 and 16 to be adhesively secured together beneath the operating table to hold the strap 12 taut, by placing the adhesive layers 22 and 24 in overlapping contact and to be released when the ends 14 and 16 are pulled apart with a force sufficient to overcome the adhesive bond between the layers 22 and 24. The length of the adhesive areas on either or both of ends 14 and 16 can vary to assure that a single device 10 can be used with various sizes and types of operating tables, and the release sheets 26 can be unitary or made of multiple parts. Similarly, the adhesive layers 22 and 24 need not overlap in use in that layer 22 can adhere to any portion of surface 20 while layer 24 can adhere to any portion of surface 18.

As shown in FIG. 1, a superior rectus bridle suture fixator 30 is provided on the device 10 and includes a fixation surface, or layer, 32 of activated adhesive disposed on the upper surface 18 centrally between the ends 14 and 16 and a cover sheet 34 disposed over the fixation surface 32. A lower face 36 of the cover sheet 34 is at least coextensive in area with the fixation surface 32 to completely cover the fixation surface, and a layer 38 of activated adhesive is provided on the lower face 36 for being releasably, adhesively secured to the fixation surface 32. An upper face 40 of the cover sheet 34 has a non-adhesive surface. The cover sheet 34 can be manually grasped and peeled away from the strap 12 with a force sufficient to overcome the adhesive bond between the fixation surface 32 and the adhesive layer 38 to reveal all or a selected part of the fixation surface 32 for fixation of superior rectus bridle sutures thereon. The cover sheet 34, once removed in whole or in part from the strap 12, can be re-secured on the strap by pressing the adhesive layer 38 against the fixation surface 32.

Preferably, the strap 12 is made of a thin, sterile, paper or cloth fabric or the like, with one preferred material being Dermicel Hypoallergenic Tape manufactured by Johnson & Johnson. The cushion 28 is preferably made from a sterile, soft material, such as gauze and the like, capable of cushioning and protecting a patient's forehead when the strap 12 is tightened around the patient's head and the operating table, and the cushion is preferably sized to cover a substantial portion of a patient's forehead laterally. The length of the strap 12 is selected to allow the strap to be used with various width operating tables to encircle a patient's head and the operating table laterally while permitting a generous overlap of the ends 14 and 16 beneath the operating table, such that the ends 14 and 16 can be overlapped a greater or lesser extent to accommodate operating tables of diverse widths. The adhesive layers 22 and 24 are sufficiently large in surface area to ensure secure attachment of the ends 14 and 16 and to permit adjustment of the overlap for different sizes of operating tables while maintaining the integrity of the attachment at the ends. The fixation surface 32 is preferably large enough in surface area to offer a range of fixation sites for superior rectus bridle sutures in either of a patient's eyes and to ensure secure fixation of bridle sutures thereon. According to a preferred embodiment, the strap 12 has an overall length of approximately 65 inches and a width of approximately 3 inches; the adhesive layers 22 and 24 extend transversely the full width of the strap, i.e. approximately 3 inches, and lengthwise along the strap from the ends 14 and 16, respectively, approximately 20 inches; the cushion 28 extends transversely the full width of the strap and lengthwise along the strap approximately 10 inches; the fixation surface 32 extends transversely the full width of the strap and lengthwise along the strap approximately 10 inches; and the head stabilizer and superior rectus bridle suture fixator is sterile and disposable for single patient use.

Another embodiment of the present invention is shown in FIG. 3 and includes a head stabilizer and superior rectus bridle suture fixator device 40 having essentially the same construction as the head stabilizer and superior rectus bridle suture fixator device 10 except that no cushion is provided on the lower surface 20 of the strap 12, and the adhesive layers 22 and 24 are replaced by strips 42 and 44 of cooperative, interlockingly engagable material as fasteners on the ends 14 and 16, respectively. Preferably, the strips 42 and 44 are formed, respectively, of complementary hook and loop type interlocking material, such as Velcro®.

In operation, as shown in FIGS. 4-6, the head stabilizer and superior rectus bridle suture fixator device is utilized during eye surgery by positioning the lower surface 20 of the strap 12 over the frontal bone, or forehead, 46 of a patient lying in a supine position on an operating table 48 with the back of the patient's head supported on the operating table. If the patient's head has not previously been draped for surgery, the head stabilizer and superior rectus bridle suture fixator device 10 is utilized, and the cushion 28 is placed directly upon the patient's forehead 46 to extend laterally along the patient's forehead as shown in FIGS. 5 and 6. If a surgical drape 50 has already been positioned over the head of the patient, as shown in FIG. 4, the head stabilizer and superior rectus bridle suture fixator device 40 can be used since a cushion may not be necessary, and a portion of the lower surface 20 disposed centrally between the ends 14 and 16 is placed over the drape 50 to extend laterally along the patient's forehead. The strap 12 is positioned to extend from the patient's forehead over lateral sides of the patient's head and the operating table as shown in FIGS. 5 and 6. When utilizing the head stabilizer and superior rectus bridle suture fixator device 10, the release sheets 26 are manually grasped and pulled away from the strap 12 with force sufficient to overcome the bond between the sheets 26 and the adhesive layers 22 and 24, respectively. The patient's head is properly positioned on the operating table 48 to optimize exposure of the eye undergoing surgery, and the ends 14 and 16 of the strap are positioned in overlapping arrangement beneath the operating table 48. The ends 14 and 16 are pulled to tighten the strap around the patient's head and the operating table laterally and, with the strap held taut, the adhesive layers 22 and 24 are placed in overlapping contact adjacent a lower surface of the operating table 48 to secure the strap in a position tightly encircling the patient's head and the operating table. Once the head stabilizer and superior rectus bridle suture fixator device 10 has been secured, the surgical drape 50 may be placed over the head stabilizer and bridle suture fixator device 10 to cover the patient's head and face and provide a sterile field for surgery as shown in FIGS. 5 and 6. When utilizing the head stabilizer and superior rectus bridle suture fixator device 40, the strap 12 is positioned over the drape 50 to encircle the patient's head and the operating table laterally, and the ends 14 and 16 are secured beneath the operating table with the fasteners 42 and 44.

After the patient's head has been satisfactorily stabilized, an opening 51 is made in the drape 50 to provide access to the patient's eye. With the patient under a local anesthetic, a surgeon approaches the eye from the top of the patient's head and over the patient's forehead, with the eyelids held apart by a clip 52 as shown in FIGS. 4 and 5. Utilizing a surgical needle having a length of suture material attached thereto, a bridle suture 54 is formed in the patient's eye as best shown in FIG. 4. In forming the bridle suture 54, the needle is inserted through the conjunctiva at an entry point 56 located approximately 8 to 10 mm behind the limbus and laterally of the superior rectus 58, the superior rectus is grasped with a muscle forceps and lifted outwardly from the eye, the needle is inserted under the raised superior rectus, and the needle and suture material are pulled through the conjunctiva to exit the eye at an exit point 60 disposed laterally of the superior rectus such that the suture material extends under the superior rectus laterally, or transversely. Free ends 62 of the suture material that extend from the entry and exits points exteriorly of the eye are grasped and pulled with desired tension in the direction of the patient's forehead to hold the superior rectus and optimally position the eye for surgery. The cover sheet 34 is manually grasped and peeled away from the strap 12 to expose at least a portion of the fixation surface 32. Depending on whether the sutured eye is the right or left eye of the patient, a right or left side of the cover sheet 34 is peeled away to expose a portion of the fixation surface 32 closest to the sutured eye. With the eye optimally positioned and the desired tension maintained on the ends 62, the ends 62 are positioned over the fixation surface 32 and are pressed thereagainst to be secured thereon by virtue of the adhesive bonding characteristics of the fixation surface. The ends 62 extend across the width of the fixation surface 32 providing continuous fixation therealong. The cover sheet 34 can be folded back over the fixation surface 32 to cover the ends 62 fixated thereon, and the adhesive layer 38 on the cover sheet adheres to the fixation surface 32 and the ends 62. If the eye is not satisfactorily positioned, the cover sheet 34 can be lifted and the ends 62 grasped and pulled away from the fixation surface 32. Once released from the fixation surface 32, the ends 62 can be manipulated to produce a different tension and/or angle to establish a more favorable position for the eye, and the ends 62 can be resecured on the fixation surface 32 to maintain the adjusted position for the eye. With both the head and the eye stabilized, eye surgery, and in particular cataract surgery, can be performed by the surgeon using standard techniques to introduce instruments into the eye to remove the cataractous natural lens. If, during the course of surgery, eye position needs to be altered, the tension and/or fixation site for the superior rectus bridle suture 54 can be changed to optimize the position of the eye.

By stabilizing a patient's head relative to an operating table during cataract surgery, the present invention allows cataract surgery to be performed with greater precision, less difficulty and increased confidence while avoiding adverse complications and consequences of surgery. The present invention is particularly advantageous for cataract removal using phacoemulsification. By preventing lateral and forward movement of the patient's head during cataract surgery, the present invention ensures proper placement of surgical instruments utilized in cataract surgery while allowing the use of a local anesthetic. Additionally, the present invention allows a patient's head to be positioned on an operating table to optimize exposure of the eye while maintaining the optimal head position. The superior rectus bridle suture fixator 30 enhances eye surgery by allowing superior rectus bridle sutures to be fixated with controlled, uniform tension and to be easily adjusted during eye surgery to vary the tension and fixation site of the bridle sutures to optimally position the eye. The bridle suture fixator allows superior rectus bridle sutures in either of the patient's eyes to be fixated with equal facility without obstructing the surgical field and without the need for clamps, tape and other extraneous devices. The cover 34, when disposed over the fixated ends 62, protects the fixated ends and inhibits inadvertent removal or displacement of the ends from a selected fixation site on the fixation surface. The head stabilizer and bridle suture fixator device is comfortable for the patient, easy to use under the time constraints of surgery, adaptable for use on diverse sizes of operating tables and is well suited for disposability, or single-patient use. When tightened over the surgical drape 50, the head stabilizer and bridle suture fixator device includes the additional advantages of securing the drape in place, enhancing the sterility of the surgical field and improving access to the bridle suture fixator 30 for adjusting eye position during surgery.

Having described preferred and alternative embodiments of a new and improved head stabilizer and superior rectus bridle suture fixator device for use in eye surgery, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A method of performing eye surgery on a patient comprising the steps of positioning a patient on a supine positin on an operating table;

covering the patient's head with a surgical drape;

stabilizing the patient'head by positioning a strap having opposing ends over the surgical drape, placing the strap along the patient's forehead and around the patient's head and the operating table to tightly encircle the patient's head and the operating table laterally and securing the opposing ends to hold the strap in the tightly encircling position to prevent forward and lateral movements of the patient's head relative to the operating table; and performing a surgical procedure on an eye while the patient's head is stabilized.

2. A method of performing eye surgery on a patient comprising the steps of supporting the patient's head;

position an adhesive fixation surface on the patient's forehead;

securing the fixation surface against movement relative to the patient's forehead;

passing a bridle suture under the superior rectus of the patient's eye;

positioning the eye with the superior rectus bridle suture;

removing a cover removably secured on the fixation surface to expose at least a portion of the fixation surface; and fixating the superior rectus bridle suture with controlled tension the fixation surface to maintain the position of the eye.

3. A method as recited in claim 2 further including, after said fixating step, the step of replacing the cover on the fixation surface to further fixate the superior rectus bridle suture.

4. A method as recited in claim 3 wherein said securing step includes providing a strap having the fixation surface thereon and securing the strap around the patient's head laterally.

5. A system for performing eye surgery comprising an operating table for supporting a patient in a supine position, a surgical drape for covering the patient's head with an opening exposing an eye to be operated, and a head stabilizer device for holding the patient's head in a stabilized non-moving position, said head stabilizer device extending across the forehead of the patient and around the operating table and having opposing ends with means on said opposing ends for fastening said opposing ends together to hold the head of the patient against the operating table, said surgical drape being disposed between said head stabilizer device and the head of the patient whereby said head stabilizer device holds said surgical drape in position on the head of the patient.

* * * * *